US008512693B2

(12) United States Patent
Capito et al.

(10) Patent No.: US 8,512,693 B2
(45) Date of Patent: Aug. 20, 2013

(54) SELF-ASSEMBLING MEMBRANES AND RELATED METHODS THEREOF

(75) Inventors: Ramille M. Capito, Lake in the Hills, IL (US); Helena S. Azevedo, Braga (PT); Samuel I. Stupp, Chicago, IL (US)

(73) Assignee: Northwestern University, Evanston, IL (US)

( * ) Notice: Subject to any disclaimer, the term of this patent is extended or adjusted under 35 U.S.C. 154(b) by 477 days.

(21) Appl. No.: 12/031,421

(22) Filed: Feb. 14, 2008

(65) Prior Publication Data

US 2008/0199431 A1    Aug. 21, 2008

Related U.S. Application Data

(60) Provisional application No. 60/901,612, filed on Feb. 14, 2007.

(51) Int. Cl.
*C12N 11/00* (2006.01)
*A61K 35/00* (2006.01)
*A61K 47/00* (2006.01)
*A61P 43/00* (2006.01)

(52) U.S. Cl.
USPC .......................... 424/93.1; 435/174; 514/772

(58) Field of Classification Search
None
See application file for complete search history.

(56) References Cited

U.S. PATENT DOCUMENTS

| 6,780,507 | B2 | 8/2004 | Toreki | |
|---|---|---|---|---|
| 7,223,571 | B2 | 5/2007 | Deangelis | |
| 2004/0077540 | A1 | 4/2004 | Quay | |
| 2005/0186261 | A1 | 8/2005 | Avelar | |
| 2005/0208100 | A1 | 9/2005 | Weber | |
| 2006/0002903 | A1* | 1/2006 | Chaikof et al. | 424/93.7 |

OTHER PUBLICATIONS

Hillberg et al (Biomacromolecules. 2006; 7:2742-2750).*
Lavelle et al (Journal of Membrane Science. 2005; 253: 49-56).*
Harrington et al. (J. Biomed. Mater. Res. 2006; 78A: 157-167).*
Aizenberg, J., et al., "Controlling local disorder in self-assembled monolayers by patterning the topography of their metallic supports," Nature 394, 868 (Aug. 27, 1998).
Bowden, N., et al., "Self-Assembly of Mesoscale Objects into Ordered Two-Dimensional Arrays," Science 276, 233 (Apr. 11, 1997).
Decher, G., "Fuzzy Nanoassemblies: Toward Layered Polymeric Multicomposites," Science 277, 1232 (Aug. 29, 1997).
Deserno, M., H.H. von Grunberg, "Osmotic pressure of charged colloidal suspensions: A unified approach to linerized Poisson-Bolzmann Theory," Phys Rev E Stat Nonlin Soft Matter Phys 66, 011401 (Jul. 2002).
Hartgerink, J.D., et al., "Self-Assembly and Mineralization of Peptide-Amphiphile Nanofibers," Science 294, 1684 (Nov. 2001).
International Search Report and Written Opinion, PCT/US2008/53990 dated Sep. 8, 2008.
Maoz, R., et al., "Self-replicating amphiphilic monolayers," Nature 384, 150 (Nov. 14, 1996).
Ohkawa, K., et al., "Preparation and Characterization of Chitosan-Gellan Hybrid Capsules Formed by Self-Assembly at an Aqueous Solution Interface," Macromolecular Materials and Engineering 289, 33 (Jan. 21, 2004).
Pirondini, L., et al., "Design and self-assembly of wide and robust coordination cages," PNAS 99, 4911 (Apr. 16, 2002).
Prokop, A., et al., "Water Soluble Polymers for Immunoisolation II: Evaluation of Multicomponent Microencapsulation Systems," Adv. Polym. Sci., 1998, 136:53-73.
Rajangam, K., et al. "Heparin Binding Nanostructures to Promote Growth of Blood Vessels," Nano Letters 6, 2086 (Sep. 13, 2006).
Schwartz, D.K., et al., "Surface Order and Stability of Langmuir-Blodgett Films," Science 257, 508 (Jul. 24, 1992).
Silva, G.A., et al., "Selective Differentiation of Neural Progenitor Cells by High-Epitope Density Nanofibers," Science 303, 1352 (Feb. 2004).
Storrie, H., et al., "Supramolecular crafting of cell adhesion," Biomaterials 28, 4608 (Nov. 2007).
Wen, S., et al., "Microcapsules through polymer complexation," Biomaterials, 12, 374 (May 1991).
Whitesides, G.M., et al., "Wet Chemical Approaches to the Characterization of Organic Surfaces: Self-Assembled Monolayers, Wetting, and the Physical-Organic Chemistry of the Solid-Liquid Interface," Langmuir 6, 87 (Jan. 1990).
Yamamoto, H., et al., "Polyion Complex Fiber and Capsule Formed by Self-Assembly of Poly-L-lysine and Gellan at Solution Interfaces," Journal of Applied Polymer Science 79, 437 (Jan. 18, 2001).
Yamamoto, H., et al., "Polyion complex fiber and capsule formed by self-assembly of chitosan and gellan at solution interfaces," Macromolecular Chemistry and Physics 201, 84 (Jan. 2000).
Zasadzinski, J.A., et al., "Langmuir-Blodgett Films," Science 263, 1726 (Mar. 25, 1994).

* cited by examiner

*Primary Examiner* — Scott Long
(74) *Attorney, Agent, or Firm* — Casimir Jones S.C.

(57) ABSTRACT

The present invention relates to self-assembling membranes. In particular, the present invention provides self-assembling membranes configured for securing and/or delivering bioactive agents. In some embodiments, the self-assembling membranes are used in the treatment of diseases, and related methods (e.g., diagnostic methods, research methods, drug screening).

17 Claims, 4 Drawing Sheets

SELF-ASSEMBLING MEMBRANES AND RELATED METHODS THEREOF

This application claims priority to provisional patent application 60/901,612, filed Feb. 14, 2007, which is herein incorporated by reference in its entirety.

This invention was made with government support by the Department of Energy (grant DE-FG02-00ER45810), the National Institutes of Health (grants 5-R01-EB003806, 5-R01-DE015920, 5-P50-NS054287), and the National Science Foundation (grant DMR-0605427). The government has certain rights in the invention.

FIELD OF THE INVENTION

The present invention relates to self-assembling membranes. In particular, the present invention provides self-assembling membranes configured to encapsulate and/or deliver bioactive agents. In some embodiments, the self-assembling membranes are used in the treatment of diseases, and related methods (e.g., diagnostic methods, research methods, drug screening).

BACKGROUND

Polyelectrolyte hydrogel-based membranes were pioneered by Chang (see, T. M. S. Chang, Artificial Cells, Charles C. Thomas, Spring field IL, 1967, pp. 524-525) in the artificial cell field. This type of microcapsule is comprised of an interfacial film formed between two polyelectrolytes of opposite charge (polyanion and polycation mixtures). The obtained thin film membrane is on the order of a cell in thickness and forms the outer wall of the microcapsule. The capsule core containing the cells, may be either fluid-filled or an immobilizing hydrogel. Multicomponent blends of synthetic, semi-synthetic and naturally occurring macromolecules have also been evaluated for the preparation of immunoisolation barriers for pancreatic islets (A. Prokop, et al., Adv. Polym. Sci., 1998, 136:53-73). Natural occurring polyanions include several polysaccharides (e.g. alginate, carboxymethyl cellulose, carrageenan, cellulose sulfate, gellan gum, gum arabic, heparin, hyaluronic acid, xanthan, carrageenan, dextran sulfate), while the synthetic polyanions can be made of polyvinylsulfate, polyglutamic acid, polystyrene sulfonate, polyvinylsulfonic acid. Polycations include naturally occurring (e.g. chitosan) and synthetic (e.g. polylysine, polyacrylamide, polyallylamine, polyamide, polyethyleneimine).

The majority of the mentioned capsules were either not sufficiently mechanically stable or suffered from other surface or matrix related deficiencies. These deficiencies include poor morphology, such as capsule sphericity and surface smoothness, which is a result of an osmolar imbalance. Membranes are also often leaky (an internal polymer slowly diffuses out through the capsule wall) or shrink in either PBS or in culture media over a period of a few hours. In order to improve the existing binary capsules several approaches have been considered and tested, like capsule coating, crosslinking, chemical adjustment of charge density, combination of low and high molecular weight polyelectrolytes, adjustment of osmotic pressure, polymer grafting, polymer blending, and processing.

Alginate has been a common material employed for microcapsule fabrication to date. Alginate, a negatively-charged polysaccharide, can either be used alone, or in conjunction with positively-charged polylysine to form alginate-polylysine polyelectrolyte complexes. Alginate itself may be ionically crosslinked by divalent cations such as calcium and barium. Although the encapsulating method based on ionic crosslinking of alginate (a polyanion) with polylysine or polyornithine (polycation) offers relatively mild encapsulating conditions and quite stable membranes, their mechanical properties and long-term stability are poor. Moreover, these polymers when implanted in vivo, are susceptible to cellular overgrowth, which restricts the permeability of the microcapsule to nutrients, metabolites, and transport proteins from the surroundings, leading to starvation and death of encapsulated cells.

Methods for polymerization of macromers using visible or long wavelength ultraviolet light (low UV light, 320 nm or greater) have been described (see, e.g., U.S. Pat. No. 6,911, 227). In such methods, polymerization of macromers using visible or long wavelength ultraviolet light is used to encapsulate or coat either directly or indirectly living tissue with polymeric coatings which conform to the surfaces of cells, tissues or carriers under rapid and mild polymerization conditions: polymers are formed from non-toxic pre-polymers (macromers) that are water-soluble or substantially water soluble and too large to diffuse into the cells to be coated. Examples of macromers include highly biocompatible PEG hydrogels, which can be rapidly formed in the presence or absence of oxygen, without use of toxic polymerization initiators, at room or physiological temperatures, and at physiological pH.

Polymerization may be initiated using non-toxic dyes such as methylene blue or eosin Y, which are photopolymerizable with visible or low UV light. The process is non-cytotoxic because little light is absorbed by cells in the absence of the proper chromophore. Cells are largely transparent to this light, as opposed to short wavelength UV radiation, which is strongly absorbed by cellular proteins and nucleic acids and can be cytotoxic. Low levels of irradiation (5-500 mW) are usually enough to induce polymerization in a time period of between milliseconds to a few seconds for most macromers. In order to encapsulate living cells for implantation, the polymerization/gelling conditions must not destroy the living cells, and the resulting polymer-coated cells must be biocompatible.

The aforementioned encapsulation methods present several problems and limitations, including the use of methods and/or materials which are thrombogenic or unstable in vivo, or require polymerization conditions which tend to destroy living cells or biologically active molecules; for example, short wavelength ultraviolet radiation (see, e.g., U.S. Pat. No. 6,780,507). In addition, the use of polyelectrolyte hydrogel membranes has been limited due to their weak mechanical strength and sealing problems.

Improved supramolecular membranes for encapsulating and delivering materials are needed.

SUMMARY OF THE INVENTION

After several decades of strong interest in self-assembly, an understanding of this bioinspired phenomenon remains in early stages. Many examples of static molecular self-assembly have been reported with particular interest on ordering of molecules at interfaces or formation of nanoscale supramolecular aggregates. Experiments conducted during the course of development of embodiments for the present invention demonstrated self-assembly of macroscopic sacs and membranes of arbitrary shape at the interface between two aqueous solutions, one containing a high molecular weight polymer and the other small self-assembling molecules bearing opposite charge. The resulting macroscopic structures have a highly ordered architecture in which fairly uniform nanofiber bundles self-align and switch orientation by nearly 90 degrees as the membrane grows. It was observed that the formation of a diffusion barrier upon initial contact between the two liquids prevented chaotic mixing of the layers. Growth of the membrane is then driven by a dynamic synergy between osmotic pressure of ions and static self-assembly. The discovery of these mechanically robust and self-sealing macroscopic structures offers opportunities in many areas, including the formation of privileged environments for cells, immune barriers, new biological assays, and self-assembly of ordered thick membranes for diverse applications.

Accordingly, in certain embodiments, the present invention provides compositions comprising a self-assembling membrane having a first component comprising a high molecular weight polymer, and a second component comprising a self-assembling molecule. In some embodiments, the self-assembling molecule has an opposite charge than the high molecular weight polymer. In some embodiments, the self-assembling molecule is smaller than the high molecular weight polymer. In some embodiments, the first and second components are dissolved in an aqueous solution or an organic solvent. In some embodiments, the high molecular weight polymer is a positively or negatively charged macromolecule. In some embodiments, the high molecular weight polymer is a charged polysaccharide. In some embodiments, the polysaccharide is hyaluronic acid with a molecular weight range between approximately 200 kDa to 4 MD (e.g., 180 kDa to 5 MD; 250 kDa to 3 MD; 500 kDa to 2 MD; 1 MD to 1.5 MD). In some embodiments, the high molecular weight polymer is a viscous solution. In some embodiments, the second component comprises a negatively or positively charged self-assembling molecule. In some embodiments, the second component comprises an amphiphilic self-assembling molecule. In some embodiments, the second component comprises a self-assembling peptide molecule. In some embodiments, the second component comprises a self-assembling molecule composed of one or more alkyl tails (e.g., branched or unbranched; saturated or unsaturated) attached to a peptide sequence. In some embodiments, the second component comprises a self-assembling molecule composed of an alkyl tail having 4-20 carbons attached to a charged peptide sequence (e.g., positive charge; negative charge). In some embodiments, the second component has the ability to self-assemble into nanostructures. In some embodiments, the second component can self-assemble into nanofibers, nanotubes, nanoribbons, or nanotapes.

The self-assembling membranes are not limited to a particular interaction between the first and second components. In some embodiments, the first and second components interact to form the self-assembling membrane. The self-assembling membranes may assume any desired shape. In some embodiments, the shape of the self-assembling membrane is a self-sealing sac. In some embodiments, the shape of the self-assembling membrane is a self-sealing film. In some embodiments, the shape of the self-assembling membrane is a continuous string. The self-assembling membranes are not limited to particular formation conditions. For example, in some embodiments, the first solution component has a pH higher than approximately 3 (e.g., 2.5, 2.8, 3.1, 3.5, 4, 5, 8, 10, 12), and the second aqueous component has a pH level between approximately 4 to 7 (e.g., 3.5 to 7.5; 3.8 to 7.2; 4 to 7; 4.5 to 6.5; 5 to 6; 5.25 to 5.75). In some embodiments, the first and second solution components have opposite zeta potentials.

In some embodiments, the self-assembling membranes are configured for encapsulating one or more bioactive agents. The self-assembling membranes are not limited to encapsulating particular bioactive agents. In some embodiments, the bioactive agent includes living cells, pharmaceutical agents, imaging agents, nucleic acid, and/or polypeptides. Additional examples of bioactive agents include, but are not limited to, a dye, a probe, a nucleic acid, an enzyme, an oligonucleotide, a label, a protein, a polypeptide, a lipid, a glycoprotein, a glycolipid, pilocarpine, hydrocortisone, prednisolone, cortisone, diclofenac sodium, indomethacin, 6-methyl-prednisolone, corticosterone, dexamethasone, prednisone, penicillin, cephalosporins, bacitracin, tetracycline, doxycycline, gentamycin, chloroquine, vidarabine, salicylic acid, acetaminophen, ibuprofen, naproxen, piroxicam, flurbiprofen, morphine, cocaine, lidocaine, benzocaine, leuprolide acetate, nafarelin, a ganglioside, a nerve growth factor, fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-alpha), transforming growth factor-beta (TGF-beta), epidermal growth factor (EGF), fibroblast growth factor (FGF), interleukin-1 (IL-1), vascular endothelial growth factor (VEGF) and keratinocyte growth factor (KGF), dried bone material, methotrexate, 5-fluorouracil, adriamycin, vinblastine, cisplatin, tumor-specific antibodies conjugated to toxins, tumor necrosis factor, progesterone, testosterone, follicle stimulating hormone (FSH) (birth control, fertility-enhancement), insulin, diphenhydramine, papaverine, streptokinase, isopropamide iodide, metaproternal sulfate, aminophylline, theophylline, niacin, minoxidil, B-adrenergic blocking agent, dopamine, risperidone, naltrexone, naloxone, buprenorphine, cross-linked alginates, gelatin, collagen, cross-linked collagen, collagen derivatives, succinylated collagen or methylated collagen, cross-linked hyaluronan, chitosan, chitosan derivatives, methylpyrrolidone-chitosan, cellulose, cellulose derivatives such as cellulose acetate or carboxymethyl cellulose, dextran derivatives such carboxymethyl dextran, starch and derivatives of starch such as hydroxyethyl starch, other glycosaminoglycans and their derivatives, other polyanionic polysaccharides or their derivatives, polylactic acid (PLA), polyglycolic acid (PGA), a copolymer of a polylactic acid and a polyglycolic acid (PLGA), lactides, glycolides, and other polyesters, polyoxanones and polyoxalates, copolymer of poly(bis(p-carboxyphenoxy)propane)anhydride (PCPP) and sebacic acid, poly(L-glutamic acid), poly(D-glutamic acid), polyacrylic acid, poly(DL-glutamic acid), poly(L-aspartic acid), poly(D-aspartic acid), poly(DL-aspartic acid), polyethylene glycol, copolymers of the polyamino acids with polyethylene glycol, polypeptides, such as, collagen-like, silk-like, and silk-elastin-like proteins, polycaprolactone, poly (alkylene succinates), poly(hydroxy butyrate) (PHB), poly (butylene diglycolate), nylon-2/nylon-6-copolyamides, polydihydropyrans, polyphosphazenes, poly(ortho ester), poly(cyano acrylates), polyvinylpyrrolidone, polyvinylalcohol, poly casein, keratin, myosin, and fibrin. Additional examples of bioactive agents include, but are not limited to, fibroblasts, hepatocytes, chondrocytes, stem cells, bone marrow, muscle cells, cardiac myocytes, neuronal cells, pancreatic islet cells, tumor cells, chondrocytes, stem cells, epithelial cells, cells from neural lineages, cells derived from the liver, endothelial cells, cardiac cells, muscle cells, and osteoblasts.

The present invention is not limited to particular uses of the self-assembling membranes. In some embodiments, the present invention provides methods for delivering bioactive agents to a subject comprising: administering to the subject (e.g., a human, a rodent, a dog, etc.) a composition comprising a self-assembling membrane comprising a bioactive agent. In some embodiments, the present invention provides drug screening assays. In some embodiments, the self-assembling membranes are used to protect particular regions (e.g., transplanted cells) within a subject from the subject's immune system. In such embodiments, the self-assembling membranes may be sutured to a particular region within the subject.

BRIEF DESCRIPTION OF THE DRAWINGS

FIG. 1 shows, (A) Schematic representation of one method to form a self-sealing closed sac: an aliquot of the denser negatively charged biopolymer solution is dropped onto a positively charged peptide amphiphile (PA) solution. Upon contact, a solid membrane forms instantly at the interface between the two solutions. Over time, the polymer drop sinks deeper into the solution of small molecules, and the membrane continues to grow as the interface renews; eventually a sealed sac forms in which the entire polymer solution droplet is completely engulfed by the membrane. (B) Open and (C) closed sac made by the method described in (A) using a fluorescently-tagged hyaluronic acid (HA) solution injected into a PA solution. (D) Self-assembled sacs of varying sizes. (E) PA-HA membranes of different shapes created by interfacing the large and small molecule solutions in a very shallow template (~1 mm thick) instead of vials as shown in B and C. (E) Continuous strings pulled from the interface between the PA and HA solutions. (G-I) Confocal microscopy of the fluorescein-labeled HA component (G) and the rhodamine-labeled PA component (H) within the sac membrane. (I) Merged images demonstrates co-localization of the PA and HA molecules within the membrane. (J) Zeta potential measurements of HA and PA solutions measured over a wide range of pH values with a qualitative rating assessing the ability to form well-defined sac structures at each pH condition. In these embodiments, robust membranes only form when polymer and small molecule solutions had high zeta potentials of opposite charge.

FIG. 2 shows (A-C) Scanning electron microscopy (SEM) of the sac membrane as it forms over time (HA component side on top, PA component side on bottom): (A) 1 minute, (B) 30 minutes, and (C) 4 days. At early stages of liquid-liquid contact, SEM reveals an amorphous layer (A, B, and D, region 1) directly adjacent to a layer of parallel fibers on the PA component side (A, B, and D, region 2) (direction of the parallel fibers is indicated by arrows). Subsequently, nanofibers start to grow perpendicular to the interface forming a layer which measures 1.5 microns after 30 minutes (B, region 3) and ~20 microns after 4 days of initial contact (C, region 3). Transmission electron microscopy (TEM) of cross-sectional slices of the membrane (E and F) confirm morphologies observed in SEM (D vs. E) particularly the perpendicularly oriented nanofibers (F, arrows). The parallel fiber region between the amorphous and perpendicular fiber zones is most obvious in TEM (E, region 2). Dark regions indicate positive staining of HA by uranyl acetate and reveal the presence of macromolecules throughout the membrane structure. (G) Polymer density profile obtained by image analysis of (E) quantifying the density of dark regions across the membrane. The density profile clearly shows three independent regions: 1) a zone with an approximately constant polymer density, 2) a region of parallel fibers with a maximum in polymer density, and 3) a region of perpendicular fibers where the polymer density starts to decay with increasing distance from the amorphous region.

FIG. 3 shows (A) Tensile test data comparing the elastic modulus of the self-assembled membrane to an amorphous membrane composed of two polyelectrolytes (the biopolymers chitosan and gellan) in both the dry and hydrated states. (B and C) SEM showing the cross sections of (B) the hierarchically ordered membrane and (C) the amorphous polymer-polymer membrane (the striations in C are effects from slicing the dense membrane during sample preparation). (D) Hierarchically ordered sac formed with polydiacetylene PA containing a macroscopic defect within the membrane (see arrow). (E) Sac in (D) after the defect is repaired and the sac resealed by triggering additional self-assembly with a drop of PA (see arrow). Sacs are robust enough to withstand suturing (F) and can hold their weight without further tearing of the membrane (G). (H) TGF-β1 release from PA gel-filled sacs and PA gels as a function of time demonstrating a nearly identical protein release profile. (I) Live/Dead assay of human mesenchymal stem cells (hMSCs) cultured within the PA gel-filled sacs (green cells are live, red cells are dead) showing the majority of cells remain viable. (J) Collagen type II gene expression of hMSCs cultured within the PA gel-filled sacs in growth medium (GM), growth medium supplemented with TGF-β1 (TGF-GM), chondrogenic medium (CM), and chondrogenic medium supplemented with TGF-β1 (TGF-CM).

FIG. 4 shows a schematic illustration of the proposed model for ordered membrane formation (HA solution on top, PA solution on bottom): (A) Electrostatic attraction between oppositely charged molecules triggers the complexation and the self-assembly of PA and HA molecules upon contact of the two solutions. (B) Initial screening and self-assembly takes place at the liquid-liquid interfacial plane that results in the formation of a contact layer composed of parallel nanofibers. The contact layer stops the intermixing of both liquids and creates a diffusion barrier for long entangled polymer chains and oppositely charged PA monomer or aggregates. (B, D) Excess osmotic pressure of ions across the barrier is hypothesized to be the driving force behind the diffusion of polymer through the contact layer (yellow arrow in B indicates direction of polymer diffusion). The macromolecules reptate through the mesh of the entire diffusion barrier and subsequently form "stubs" within the PA solution. (C, E) Polymer stubs attract PA aggregates (red arrows in C) and nucleate the self-assembly of nanofibers oriented perpendicular to the interface. (F) Over time, growth and crowding of the nanofibers leads to greater alignment and densification as well as membrane thickening.

DETAILED DESCRIPTION OF THE INVENTION

The organization of molecules at interfaces has been a phenomenon of great interest over several decades given its importance in the preparation of chemically defined surfaces and ordered materials. One classical system is the Langmuir-Blodgett (LB) film in which molecules are ordered by compression at an air-water interface, followed by deposition of multilayers through repeated immersion of a solid substrate in the liquid phase (see, e.g., D. K. Schwartz, et al., Science 257, 508 (Jul. 24, 1992); J. A. Zasadzinski, et al., Science 263, 1726 (Mar. 25, 1994)). Another widely studied system is the self-assembling monolayer (SAM) formed at a solid-liquid interface by the reaction and self-ordering of dissolved molecules on a solid surface (see, e.g., J. Aizenberg, et al., Nature 394, 868 (Aug. 27, 1998); R. Maoz, et al., Nature 384, 150 (Nov. 14, 1996); G. M. Whitesides, et al., Langmuir 6, 87 (January, 1990)). Other systems include the formation of molecular complexes or solid objects at the interface of two immiscible liquids (see, e.g., N. Bowden, et al., Science 276, 233 (Apr. 11, 1997); L. Pirondini et al., PNAS 99, 4911 (Apr.

16, 2002)), and electrostatic layer-by-layer deposition of amorphous polymers at the solid-liquid interface by alternating their charge (see, e.g., G. Decher, Science 277, 1232 (Aug. 29, 1997)). Hybrid strategies combining features of the LB film, the SAM, and the layer-by-layer approach have also been developed. The SAM has monolayer character with very high order parameter, and the other systems require repeated mechanical action to generate thicker films with or without order. Ordered monolayers have been important as the strategy of choice to generate chemically defined surfaces for both science and applications. The multilayered films with nanoscale periodicity have been important as a source of materials with novel properties, particularly for electronic and optical devices.

In some embodiments, the present invention provides self-assembling ordered materials (e.g., self-assembled materials well beyond the nanoscale). The present invention is not limited to particular self-assembling ordered materials. In some embodiments, the self-assembling materials comprise ordered materials at the interface between two aqueous solutions. The self-assembling ordered materials are not limited to particular types of aqueous solutions. In some embodiments, the aqueous solution include a combination of 1) viscous containing high molecular weight charged macromolecules, and 2) small self-assembling molecules of opposite charge. In some embodiments, the self-assembling ordered materials are self-assembling membranes.

The self-assembling ordered materials (e.g., self-assembling membranes) of the present invention provide an improvement over previous descriptions of solids formed between oppositely charged macromolecules (see, e.g., K. Ohkawa, et al., Macromolecular Materials and Engineering 289, 33 (Jan. 21, 2004); S. Wen, et al., Biomaterials 12, 374 (May, 1991); H. Yamamoto, et al., Journal of Applied Polymer Science 79, 437 (Jan. 18, 2001); H. Yamamoto, et al., Macromolecular Chemistry and Physics 201, 84 (January, 2000)). Indeed, the self-assembling ordered materials (e.g., self-assembling membranes) of the present invention are, in some embodiments, permeable to large molecules (e.g., proteins), stable in water without the use of cross-linking chemistry, are readily repaired, are mechanically robust in both dry and hydrated states, and have an capability to self-seal defects instantly by self-assembly. The self-assembling ordered materials (e.g., self-assembling membranes) of the present invention are not limited to particular types of 1) viscous solutions containing high molecular weight charged macromolecules, and 2) small self-assembling molecules of opposite charge. Experiments conducted during the course of development of embodiments for the present invention demonstrated that self-assembling ordered materials were generated upon combination of, for example, an aqueous solution of a peptide amphiphile (PA), which consists of an alkyl tail having approximately 16 (e.g., 12, 13, 14, 15, 16, 17, 18, 19, 20, 30, 50, 100) carbon atoms that may be linear or branched, saturated or unsaturated covalently linked to a peptide sequence (e.g., containing arginines, histidines, lysines, serines, glutamines, alanines, glycines, isoleucines, leucines, methionines, phenylalanines, prolines, tryptophans, and/or valines) (e.g. VVVAAAKKK) at approximately a 0.5-4 wt % concentration (e.g., 0.3-4.2%; 0.4-2%; 0.5-1.5%; 1-1.25%) with approximately a 0.1-2 wt % aqueous solution (e.g., 0.01%-4%; 0.05%-3.75%; 0.1%-2%; 0.5%-1.5%; 1%-1.25%) of the naturally occurring high molecular weight polysaccharide hyaluronic acid (HA). In some embodiments, the average molar mass for HA was 1.76 MD, although other sizes may be used (e.g., 180 kDa to 5 MD; 250 kDa to 3 MD; 500 kDa to 2 MD; 1 MD to 1.5 MD).

Accordingly, in some embodiments, the viscous solution containing high molecular weight charged macromolecules used in the self-assembling ordered materials (e.g., self-assembling membranes) comprises HA. In some embodiments, the small self-assembling molecules of opposite charge used in the self-assembling ordered materials (e.g., self-assembling membranes) comprises PA.

The self-assembling ordered materials (e.g., self-assembling membranes) are not limited to a particular type of PA. In some embodiments, PAs are small synthetic molecules containing a hydrophobic alkyl segment covalently grafted to a short peptide. In some embodiments, the PA comprises an alkyl tail of 16 carbons attached to the peptide sequence $V_3A_3K_3$. In some embodiments, the PAs self-assemble into high aspect ratio nanofibers (see, e.g., J. D. Hartgerink, et al., Science 294, 1684 (November, 2001); G. A. Silva et al., Science 303, 1352 (February, 2004); K. Rajangam et al., Nano Letters 6, 2086 (Sep. 13, 2006); H. Storrie et al., Biomaterials 28, 4608 (November, 2007), each of which is herein incorporated by reference in their entireties). In some embodiments, the PAs have a tolerance of arbitrary domains past a β-sheet forming sequence making them useful in, for example, biological signaling. In some embodiments, the PAs include small (<2 kD) synthetic, peptide-based molecules that typically comprise, for example, an alkyl tail, a β-sheet forming peptide segment, and a bioactive peptide group that self-assemble into nanofibers containing a hydrophobic core by adjustment of pH or addition of multivalent ions. In some embodiments, in vivo ion concentrations present in physiological fluids are sufficient to induce gelation of PAs to form structures of similar features of the extracellular matrix (e.g., a minimally invasive procedure is used by simple injection of the PA solution within a treatment site). In some embodiments, the PAs serve as an analog of the extracellular matrix (ECM), for example, by successfully supporting cell attachment and proliferation, ECM signaling activity, and binding of proteoglycan matrix molecules. In some embodiments, the PAs are synthesized to contain growth factor binding groups. In some embodiments, the PAs are covalently linked to drugs. In some embodiments, the capability of easily manipulating the PA molecules to create self-assembled structures with a variety of different bioactive moieties on the molecular scale render such materials candidates for biomedical applications.

The materials (e.g., self-assembling membranes) are not limited to a particular type of polysaccharide. In some embodiments, the polysaccharide is a negatively charged macromolecule with a disaccharide repeat unit of N-acetyl-glucosamine and glucuronic acid, present in mammalian extracellular matrix.

The self-assembling ordered materials (e.g., self-assembling membranes) are not limited to particular assembly conditions. In some embodiments, adjustment of pH results in self-assembling ordered materials (e.g., self-assembling membranes) having different consistencies. For example, in some embodiments, at specific pH conditions, a solid material with structural order forms instantly upon contact between HA and PA. In some embodiments, immiscibility of the HA and PA solutions is important for membrane formation at the interphase and occurs when the PA solution is, for example, at pH 4-7 and the HA solution is, for example, at pH<10. In some embodiments, the immiscibility and the electrostatic interaction of the HA and PA play a major role in forming the ultra-thin membrane at the interphase. In some embodiments, upon contact, the HA molecules serve as a nucleation template for PA fiber formation. The resulting organized fiber network creates structures that possess unique mechanical and biochemical properties that are, for example, different from other films or structures made from HA or PA alone.

Figure 1:
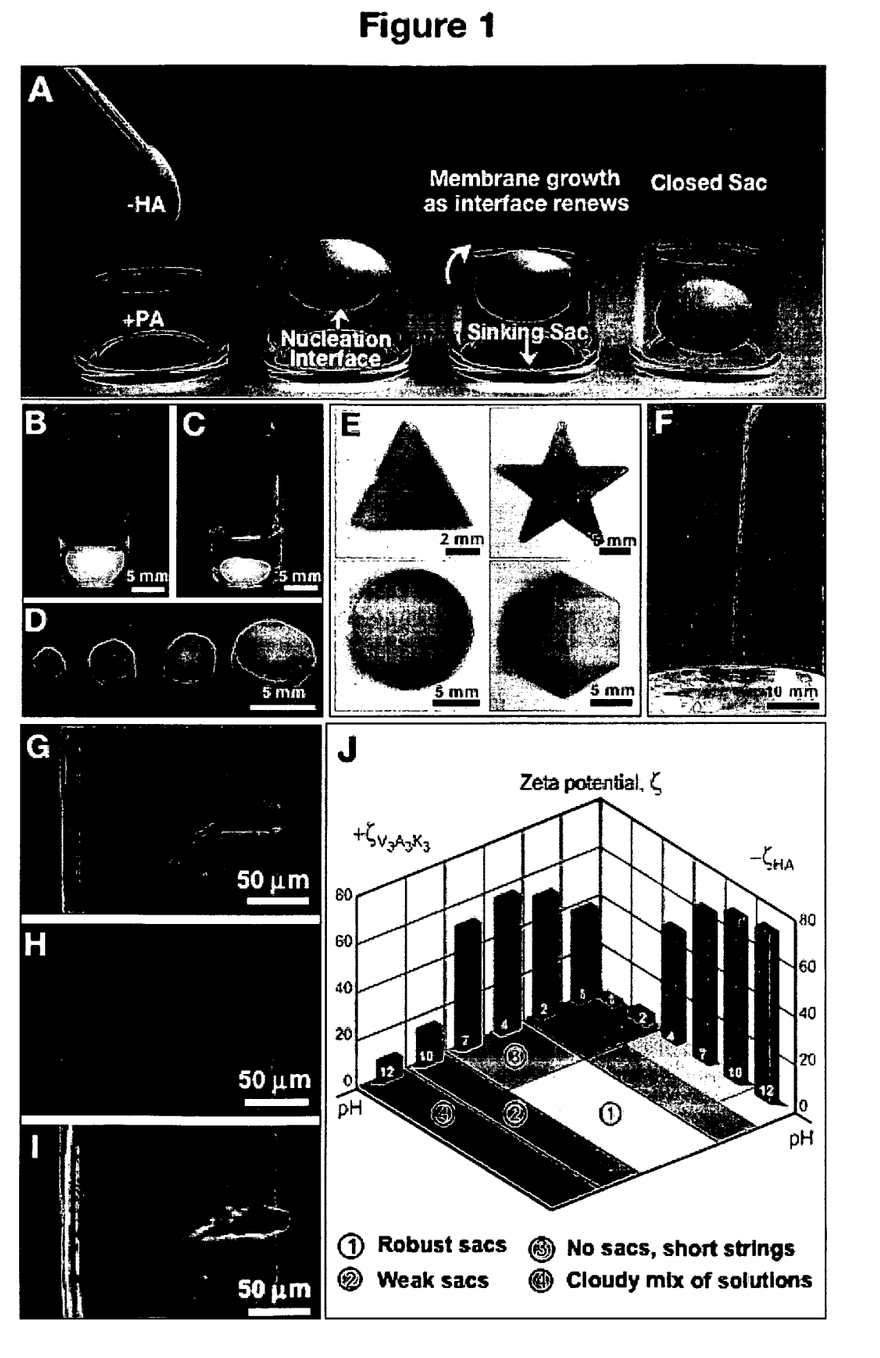

The materials (e.g., self-assembling membranes) are not limited to particular size dimensions. In some embodiments, the materials (e.g., self-assembling membranes) grow to macroscopic dimensions with a high degree of hierarchical order across scales. The materials are not limited to a particular structure. In some embodiments, the materials are assembled into various types of structures including, but not limited to, self-sealing sacs (see, e.g., FIGS. 1B-D), films with tailorable size and shape (see, e.g., FIG. 1E), and continuous strings (see, e.g., FIG. 1F).

Experiments conducted during the course of development of embodiments for the present invention demonstrated that combination of the dilute solutions of PA with the high molecular weight HA in equal volumes resulted in instant formation of a solid membrane localized at the interface between the two liquids. It was shown that placement of the denser HA solution on top of the PA solution resulted in the sinking of the HA fluid into the PA component, causing renewal of the liquid-liquid interface and continuous membrane growth until the entire volume of HA solution was completely engulfed (see, e.g., FIG. 1A). The outcome was the formation of a polymer filled sac over periods of minutes to hours depending on the volume and density of the utilized HA and PA liquids. It was also shown that closed sacs were instantly generated by injecting one solution directly into the bulk volume of the other solution (e.g., HA directly into PA; PA directly into HA) creating HA-filled or PA-filled sacs, respectively. Confocal microscopy confirmed the incorporation of both HA and PA components within the sac membrane (see, e.g., FIGS. 1G-I).

In some embodiments, the HA and PA components within the self-assembling ordered materials (e.g., self-assembling membranes) have opposite zeta potentials. The effect of zeta potential in HA and PA solutions on membrane formation was investigated during the development of embodiments for the present invention. Zeta potential measurements of 0.1 wt % HA and PA solutions were assessed over a wide pH range and the ability to form well-defined self-assembling ordered material sac structures was determined qualitatively at each pH condition by injecting an aliquot of a 0.75 wt % HA solution into an aliquot of 1 wt % PA solution. In some embodiments, it was shown that sac membranes with physical integrity were when both solutions had strong zeta potentials of opposite charge (see, FIG. 1J). The zeta potential determines the degree of stability of charged aggregates in the HA and PA solutions correlates directly to the total electrostatic charge of molecules in the presence of counter ions.

In some embodiments, a solution of the small self-assembling molecules of opposite charge may be used to repair defects within the self-assembling ordered materials (e.g., a defect in a self-assembling ordered material sac membrane). In some embodiments involving, for example, biological applications, the "sealing" capability permits injection of solutions (e.g., containing drugs, proteins, nucleic acids) and/or cells in suspension within the sac after its original formation.

The self-assembling ordered materials (e.g., self-assembling membranes) of the present invention are not limited to particular uses. In some embodiments, the self-assembling ordered materials (e.g., self-assembling membranes) are used for medical purposes. The self-assembling ordered materials can be placed directly in or on any biological system. Examples of sites the compounds self-assembling ordered materials can be placed include, but are not limited to, soft tissue such as muscle or fat; hard tissue such as bone or cartilage; areas of tissue regeneration; a void space such as periodontal pocket; surgical incision or other formed pocket or cavity; a natural cavity such as the oral, vaginal, rectal or nasal cavities, the cul-de-sac of the eye, and the like; the peritoneal cavity and organs contained within, and other sites into or onto which the self-assembling ordered materials (e.g., self-assembling membranes) can be placed including a skin surface defect such as a cut, scrape or burn area. Alternatively, the self-assembling ordered materials (e.g., self-assembling membranes) can be used to extend the viability of damaged skin. In some embodiments, the self-assembling ordered materials (e.g., self-assembling membranes) can be used in a number of different surgical procedures (e.g., cardiosurgery and articular surgery; abdominal surgery; operations performed in the urogenital regions; nerve surgery operations; opthalmological surgery; ear-nose-throat surgery).

In some embodiments, the self-assembling ordered materials (e.g., self-assembling membranes) are provided in membrane form so that the construct can also be sutured to surrounding tissue to serve as a barrier for isolating cells in vivo. For example, pancreatic islets can be self-assembling within the sacs or underneath a membrane flap so that they can deliver insulin to diabetic patients but still remain isolated and contained in a confined space in the body. Cells self-assembling within these self-assembling sacs in vitro also find use for drug diagnostic applications where the encapsulated cells can be exposed to different drug treatments in order to evaluate the cytotoxicity of drugs in development. Examples of subjects that can be treated with the self-assembling ordered materials (e.g., self-assembling membranes) include mammals such as mice, rats, cows or cattle, horses, sheep, goats, cats, dogs, and primates, including apes, chimpanzees, and humans.

The self-assembling ordered materials (e.g., self-assembling membranes) of the present invention can be delivered onto cells, tissues, and/or organs, for example, by injection, spraying, squirting, brushing, painting, coating, and the like. Delivery can also be via a cannula, catheter, syringe with or without a needle, pressure applicator, pump, and the like. The self-assembling ordered materials (e.g., self-assembling membranes) of the present invention can be applied onto a tissue in the form of a film, for example, to provide a film dressing on the surface of the tissue, and/or to adhere to a tissue to another tissue.

In some embodiments, the self-assembling ordered materials (e.g., self-assembling membranes) are used in tissue regeneration. In such embodiments, injection of the HA and PA solutions forms, for example, a thin membrane or fluid-filled or gel-filled sac at a desired tissue site. In some embodiments, the self-assembling ordered material sacs are configured to contain various growth factors known to assist in tissue regeneration. In some embodiments, the self-assembling ordered materials (e.g., self-assembling membranes) encapsulate cells that can be delivered at a defect site so as to further enhance tissue regeneration. The self-assembling ordered materials (e.g., self-assembling membranes) of the present invention can be used for treating a wide variety of tissue defects in an animal, for example, a tissue with a void such as a periodontal pocket, a shallow or deep cutaneous wound, a surgical incision, a bone or cartilage defect, bone or cartilage repair, vocal fold repair, and the like. For example, the self-assembling ordered materials (e.g., self-assembling membranes) of the present invention can be applied to a defect in bone tissue such as a fracture in an arm or leg bone, a defect in a tooth, a cartilage defect in the joint, ear, nose, or throat, and the like. The self-assembling ordered materials (e.g., self-assembling membranes) of the present invention can also function as a barrier system for guided tissue regeneration by providing a surface on or through which cells can grow.

In some embodiments, the present invention provides pharmaceutical compositions comprising self-assembling ordered materials (e.g., self-assembling membranes) and one or more bioactive agent. In some embodiments, the bioactive agent is encapsulated within the self-assembling ordered material. In some embodiments, the bioactive agent is separate from the self-assembling ordered material. In some embodiments, the pharmaceutical composition provides a system for sustained, continuous delivery of one or more bioactive agents to tissues adjacent to or distant from an application site.

The present invention is not limited to a particular type of bioactive agent. In some embodiments, the bioactive agent is capable of providing a local or systemic biological, physiological or therapeutic effect in the biological system to which it is applied. For example, in some embodiments, the bioactive agent acts to control infection or inflammation, enhance cell growth and tissue regeneration, control tumor growth, act as an analgesic, promote anti-cell attachment, and/or enhance bone growth, among other functions. In some embodiments, the bioactive agent is any therapeutic, prophylactic, pharmacological or physiological active substance, or mixture thereof, which is delivered to a subject to produce a desired, usually beneficial, effect. In one aspect, any active agent that is capable of producing a pharmacological response, localized or systemic, irrespective of whether therapeutic, diagnostic or prophylactic in nature, can be used as bioactive agents in any of the methods and pharmaceutical compositions described herein. It should be noted that the bioactive agent can be used singularly or as a mixture of two or more agents. Thus, it is possible to have two or more bioactive agents covalently attached upon encapsulation within the self-assembling ordered materials (e.g., self-assembling membranes) of the present invention. In some embodiments, the bioactive agent is a dye, a probe, a nucleic acid, an enzyme, an oligonucleotide, a label, a protein, a polypeptide, a lipid, a glycoprotein, a glycolipid, or a pharmaceutically-acceptable compound. In some embodiments, the bioactive agents include substances capable of preventing an infection systemically in the biological system or locally at the defect site, as for example, anti-inflammatory agents such as, but not limited to, pilocarpine, hydrocortisone, prednisolone, cortisone, diclofenac sodium, indomethacin, 6-methyl-prednisolone, corticosterone, dexamethasone, prednisone, and the like; antibacterial agents including, but not limited to, penicillin, cephalosporins, bacitracin, tetracycline, doxycycline, gentamycin, chloroquine, vidarabine, and the like; analgesic agents including, but not limited to, salicylic acid, acetaminophen, ibuprofen, naproxen, piroxicam, flurbiprofen, morphine, and the like; local anesthetics including, but not limited to, cocaine, lidocaine, benzocaine, and the like; immunogens (vaccines) for stimulating antibodies against hepatitis, influenza, measles, rubella, tetanus, polio, rabies, and the like; peptides including, but not limited to, leuprolide acetate (an LH-RH agonist), nafarelin, and the like. In some embodiments, the bioactive agent is a substance or metabolic precursor capable of promoting growth and survival of cells and tissues or augmenting the functioning of cells is useful, as for example, a nerve growth promoting substance such as a ganglioside, a nerve growth factor, and the like; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-alpha), transforming growth factor-beta (TGF-beta), epidermal growth factor (EGF), fibroblast growth factor (FGF), interleukin-1 (IL-1), vascular endothelial growth factor (VEGF) and keratinocyte growth factor (KGF), dried bone material, and the like; and antineoplastic agents such as methotrexate, 5-fluorouracil, adriamycin, vinblastine, cisplatin, tumor-specific antibodies conjugated to toxins, tumor necrosis factor, and the like. In some embodiments, the bioactive agent is a hormone such as progesterone, testosterone, and follicle stimulating hormone (FSH) (birth control, fertility-enhancement), insulin, and the like; an antihistamine such as diphenhydramine, and the like; a cardiovascular agent such as papaverine, streptokinase and the like; an anti-ulcer agents such as isopropamide iodide, and the like; bronchodilators such as metaproternal sulfate, aminophylline, and the like; vasodilators such as theophylline, niacin, minoxidil, and the like; central nervous system agents such as tranquilizer, B-adrenergic blocking agent, dopamine, and the like; antipsychotic agents such as risperidone, narcotic antagonists such as naltrexone, naloxone, buprenorphine; and other like substances.

In some embodiments, the bioactive agent is a pro-healing compound. Examples of pro-healing compounds include, but are not limited to, cross-linked alginates, gelatin, collagen, cross-linked collagen, collagen derivatives, such as, succinylated collagen or methylated collagen, cross-linked hyaluronan, chitosan, chitosan derivatives, such as, methylpyrrolidone-chitosan, cellulose and cellulose derivatives such as cellulose acetate or carboxymethyl cellulose, dextran derivatives such carboxymethyl dextran, starch and derivatives of starch such as hydroxyethyl starch, other glycosaminoglycans and their derivatives, other polyanionic polysaccharides or their derivatives, polylactic acid (PLA), polyglycolic acid (PGA), a copolymer of a polylactic acid and a polyglycolic acid (PLGA), lactides, glycolides, and other polyesters, polyoxanones and polyoxalates, copolymer of poly(bis(p-carboxyphenoxy)propane)anhydride (PCPP) and sebacic acid, poly (L-glutamic acid), poly(D-glutamic acid), polyacrylic acid, poly(DL-glutamic acid), poly(L-aspartic acid), poly(D-aspartic acid), poly(DL-aspartic acid), polyethylene glycol, copolymers of the polyamino acids with polyethylene glycol, polypeptides, such as, collagen-like, silk-like, and silk-elastin-like proteins, polycaprolactone, poly(alkylene succinates), poly(hydroxy butyrate) (PHB), poly(butylene diglycolate), nylon-2/nylon-6-copolyamides, polydihydropyrans, polyphosphazenes, poly(ortho ester), poly(cyano acrylates), polyvinylpyrrolidone, polyvinylalcohol, poly casein, keratin, myosin, and fibrin.

It will be appreciated that the actual preferred amounts of bioactive agents in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physician's Desk Reference, Barnhart Publishing (1999)).

In some embodiments, the self-assembling ordered materials (e.g., self-assembling membranes) are used for the delivery of living cells to a subject. The present invention is not limited to the delivery of particular types or kinds of living cells. Examples of living cells include, but are not limited to, fibroblasts, hepatocytes, chondrocytes, stem cells, bone marrow, muscle cells, cardiac myocytes, neuronal cells, or pancreatic islet cells. In some embodiments, the self-assembling ordered materials (e.g., self-assembling membranes) are used to deliver a variety of cells including, but not limited to, tumor cells, fibroblasts, chondrocytes, stem cells (e.g., embryonic, preadipocytes, mesenchymal, cord blood derived, bone marrow), epithelial cells (e.g., breast epithelial cells, intestinal epithelial cells), cells from neural lineages (e.g., neurons, astrocytes, oligodendrocytes, and glia), cells derived from the liver (e.g., hepatocytes), endothelial cells (e.g., vascular endothelial), cardiac cells (e.g., cardiac myocytes), muscle cells (e.g., skeletal or vascular smooth muscle cells), or osteoblasts. In some embodiments, the self-assembling ordered materials (e.g., self-assembling membranes) are used to deliver cells derived from cell lines or a primary source (e.g., human or animal), a biopsy sample, or a cadaver.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); and ° C. (degrees Centigrade).

Example I

This example describes general methods to create self-assembling peptide amphiphile (PA)-polymer sacs, membranes and strings. To create a self-assembling sac membrane, an aliquot of a viscous negatively charged biopolymer solution is dropped onto a positively charged PA solution. Upon contact, a solid membrane forms instantly at the interface between the two solutions. Over time, the polymer drop sinks deeper into the solution of small molecules, and the membrane continues to grow as the interface renews until the entire polymer solution droplet is completely engulfed by the membrane. Alternatively, self-assembling sacs can be made by injecting a high molecular weight polymer solution directly into the bulk PA solution or vice versa. Flat self-assembling membranes of different shapes can be created by interfacing the large and small molecule solutions in a very shallow templates (e.g., shallow templates with ~1 mm thickness). Continuous self-assembling strings can also be pulled from the interface between the PA and polymer solutions.

Example II

Figure 2:
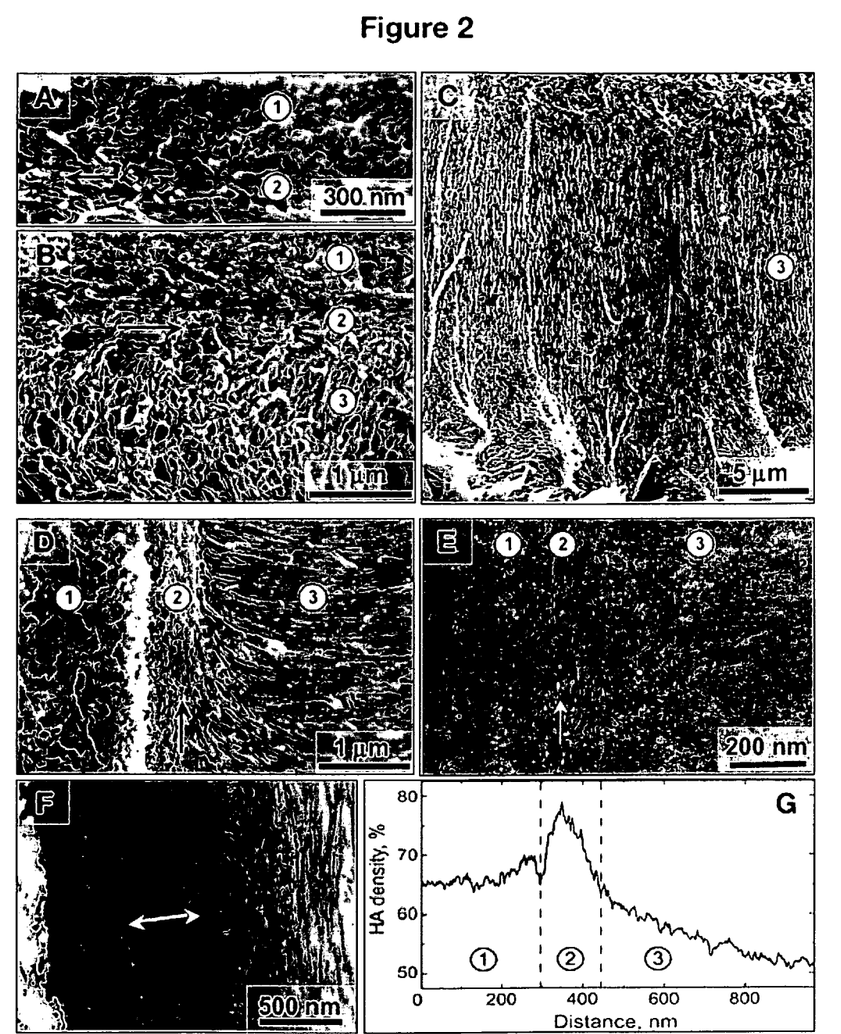

This example describes the microstructure of the PA-HA sac membranes as a function of time using electron microscopy. In the early stages of liquid-liquid contact, scanning electron micrographs revealed an amorphous layer (FIG. 2D, region 1) directly adjacent to a layer of parallel fibers on the PA solution side (FIG. 2D, region 2). Rapid diffusion of the small PA molecules into the HA solution and electrostatic complexation of both molecules resulted in the formation of the amorphous zone. It was proposed that the parallel fiber region, which measured approximately 150 nm within one minute of contact, was the result of self-assembly triggered by electrostatic screening of the amphiphiles by the negatively charged HA molecules near the interface. These early events that occurred upon contact between the two liquids established a diffusion barrier, which prevented the rapid mixing of the two miscible liquids. What followed after early contact was an ordered growth of nanofibers oriented perpendicular to the interface forming a layer which measured ~1.5 microns after 30 minutes (FIG. 2B, region 3) and ~20 microns after 4 days of initial contact (FIG. 2C, region 3).

Transmission electron microscopy (TEM) of cross-sectional slices of a hydrated membrane sample (FIGS. 2E and F) confirmed the morphologies observed by SEM (FIGS. 2D vs. 2E). TEM samples were prepared by fixing hydrated sac structures in 2% glutaraldehyde/2% paraformaldehyde and 1% osmium textroxide, dehydrated in acetone, embedded in epoxy resin, and cured. Ultrathin sections (70 nm thick) were obtained using an ultramicrotome, placed on TEM grids and stained with uranyl acetate (positive stain for HA, negative stain for PA). TEM revealed the presence of the high molar mass polymer throughout the thickness of the membrane (dark regions indicate positive staining of HA by uranyl acetate). The parallel fiber region between the amorphous layer and the perpendicular fibers was more obvious in the TEM micrographs (FIG. 2E, region 2). The HA density across the membrane shown in FIG. 2E was calculated by image analysis (FIG. 2G). The density profile showed three independent regions: 1) a region with an approximately constant polymer density, 2) the region of parallel fibers where there was a maximum in polymer density, and 3) the region of perpendicular fibers where the polymer density decayed with increasing distance from the amorphous region. The majority of region 1 where there was constant HA density was most likely excess HA from the bulk solution that is merged with a portion of the amorphous region of the membrane. The observed accumulation of HA component in the region of parallel oriented nanofibers (FIG. 2E, region 2) suggested a denser arrangement of nanostructures in that zone. It was expected that diffusion of both the large and small molecules would eventually slow down as density increased in the perpendicular fiber region. This was supported by the decrease in HA density across the region of perpendicular fibers.

Example III

This example describes the properties of the PA-HA membranes (e.g., mechanical robustness and stability of the PA-HA membranes in the hydrated state, and the self-sealing, suturing and permeability capabilities of the PA-HA membranes).

Figure 3:
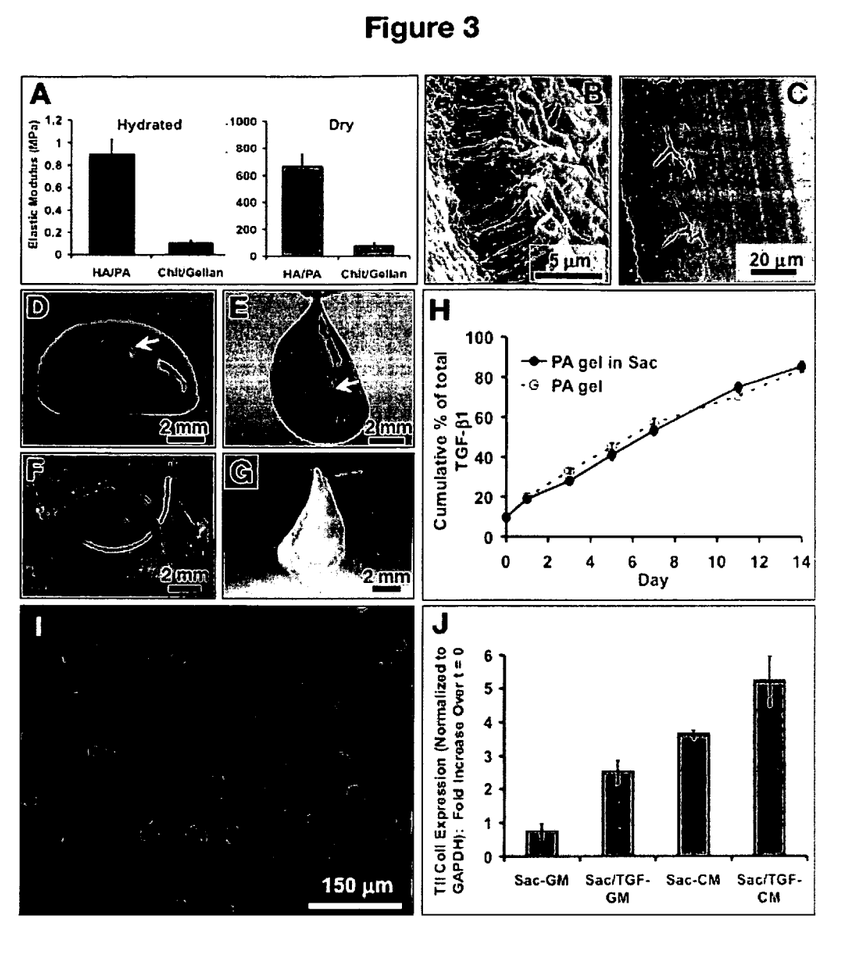

The mechanical properties of PA-HA membranes were evaluated by a tensile test in both dry and hydrated states. Rectangular samples (30×5 mm$^2$) of a mature PA-HA membrane were tensile tested in both the dry and hydrated states at room temperature using a dynamic mechanical analysis RSA III instrument (TA instruments, Delware, Del.). In the dry state, data was collected using a multiple extension mode at a crosshead rate of 0.001 mm/s. In the hydrated state, where the sample remains completely submerged in water during the test, the sample was allowed to equilibrate and then tensile tested using a crosshead rate of 0.01 mm/s. The stress was monitored as function of strain and the elastic modulus was obtained by calculating the slope of the linear region in the resulting stress-strain curves. The elastic moduli in the dry and hydrated state of the membrane were found to be about 670 and 0.9 MPa, respectively (FIG. 3A). For comparison, the moduli of membranes formed by the complexation of two oppositely charged polysaccharides, chitosan and gellan (see, e.g., K. Ohkawa, et al., Macromolecular Materials and Engineering 289, 33 (Jan. 21, 2004); H. Yamamoto, et al., Journal of Applied Polymer Science 79, 437 (Jan. 18, 2001)) (both of high molecular weight), were measured. The elastic modulus of PA-HA membranes was found to be about 9-fold higher than that of the chitosan-gellan membranes in both hydrated and dry states (FIG. 3A). In spite of their lower stiffness, SEM micrographs of the chitosan-gellan membranes (FIG. 3C) showed a dense structure compared to the PA-HA membrane (FIG. 3B). Furthermore, the chitosan-gellan membranes, swollen to about 20 times their original dry thickness, behaved more like hydrogels and fell apart over time when immersed in water. Hydrated PA-HA membranes, on the other hand, exhibited minimal dimensional change and remained very stable over months in either water or phosphate buffered saline. It was concluded that the hierarchical order in the self-assembled membrane contributed to its greater hydrolytic stability and robust mechanical properties.

It was found to be possible to instantly reseal a macroscopic hole in a polymer filled sac. Using a diacetylene PA molecule that can be polymerized after self-assembly to an intense blue color, HA-filled sacs were recreated and a macroscopic defect can be easily visualized (FIG. 3D). Since the HA component was contained within the sac, application of additional PA solution within the defect space created a new membrane segment instantly, with edges sufficiently sealed to the original sac membrane to prevent leakage of the fluid inside (FIG. 3E). In some embodiments involving, for example, biological applications, this "sealing" capability permits injection of solutions (e.g., containing drugs, proteins, nucleic acids) or cells in suspension within the sac after its original formation. Furthermore, because of the robust character, the PA-HA sacs can be easily manipulated and sutured (FIG. 3F), thereby allowing, for example, localized delivery of therapeutic factors or cells in vivo. When sutured, the sac can hold its own weight without further tearing of the membrane (FIG. 3G).

A common limitation of polyelectrolyte complexes is lack of permeability to larger molecules such as proteins and nucleic acids. The permeability capabilities of the PA-HA membrane were tested by monitoring diffusion of transforming growth factor (TGFβ-1, 25 kDa) out of a PA gel-filled sac. As a control in this experiment, a PA gel was created without the surrounding sac membrane. Sacs enclosing a PA gel and TGFβ-1 were created by mixing a ~1 wt % negatively charged PA solution ($C_{16}H_{33}V_3A_3E_3$) and TGFβ-1 (2 ng per sac) with the HA solution before injecting the mixture into the positively charged PA solution. To subsequently gel the negative PA inside, an aliquot of calcium chloride solution was placed on top of the sac. The positive calcium ions effectively penetrate the membrane and trigger self-assembly of the negative PA within the sac. PA gels without surrounding membranes were made by injecting an aliquot of the negative PA solution containing TGFβ-1 (2 ng per gel) into the calcium chloride solution. Sacs or gels containing TGFβ-1 were placed in phosphate buffered saline (PBS) for protein release studies. At various time points, aliquots of the PBS from each sample were collected and replaced and the amount of TGFβ-1 in the collected samples was determined using a human ELISA kit from BD Biosciences (San Diego, Calif.). Results over a 2-week period revealed similar TGFβ-1 release kinetics between the gels with and without the surrounding membrane structure (FIG. 3H), thus confirming the permeability of the HA-PA membrane to proteins. It was expected that tunable permeability and mechanical properties are accomplished by adjusting sac formation parameters.

Example IV

This example describes the capability of using PA-HA sacs as a matrix environment for cell encapsulation, growth, and differentiation. To investigate if the PA-HA structures support cell viability and differentiation, in vitro studies were performed using human mesenchymal stem cells (hMSCs). Human MSCs (Lonza; Walkersville, Md.) were used at passage 5. Cell encapsulation within sacs was accomplished by mixing the cell suspension with a mixture of HA and negative PA solution before being injected into the positive PA solution. The negative PA solution within the sac was gelled. Expanded hMSCs were incorporated within gel-filled sacs and cultured in growth media, growth media plus TGFβ-1 supplementation, chondrogenic media, or chondrogenic media plus TGFβ-1 supplementation. The hMSCs remained viable within the sacs (FIG. 3I) for up to 4 weeks in culture. Cell viability was determined by a Live/Dead assay kit from Molecular Probes (Eugene, Oreg.). Furthermore, real time RT-PCR results after 2 weeks in culture (FIG. 3J) revealed an upregulation in collagen type II gene expression, indicating that hMSCs were able to differentiate towards a chondrogenic phenotype within the sacs. The self-assembling sacs could therefore provide sufficient nutrient diffusion necessary for cell survival and differentiation.

Example V

This example describes a mechanism for the self-assembly of the hierarchically ordered materials (e.g., self-assembling membranes). The present invention is not limited to this particular mechanism.

Figure 4:
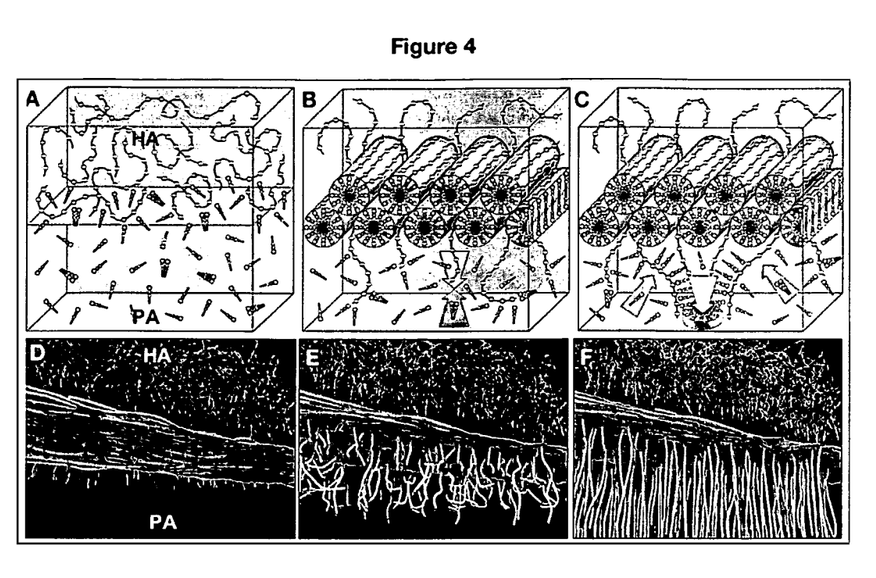

The experimental data suggest that, for example, self-assembly is a two-step process involving first the static self-assembly of a physical barrier between the two liquid components followed by growth over time of the zone with perpendicular fibers. The first step is, in some embodiments, kinetic in origin and involves rapid mixing by diffusion of molecules localized at the interface (FIG. 4A). Based on molecular weight differences, in some embodiments, the small PA molecules more readily diffuse within the polymer solution upon initial interfacial contact. Electrostatic attraction causes, in some embodiments, the initial complexation between the HA and PA molecules in the contact layer, and ionic screening by the HA molecules results in, for example, the simultaneous self-assembly of PAs into nanofibers. Since ionic screening occurs along the entire area of liquid-liquid contact, in some embodiments, self-assembly results in PA nanofibers localized at the interface (FIG. 4B). Multiple layers of these parallel nanofibers should form until screening is no longer effective. The instant formation of this contact layer creates, in some embodiments, a diffusion barrier for long entangled HA chains as well as for PA molecules or their aggregates, resulting, in some embodiments, in the physical separation of both components. Static self-assembly of the contact layer is followed, in some embodiments, by thickening and densification of the membrane through growth of fibers oriented perpendicular to the interface. Growth of the fibers, which are hybrids of HA and PA, occurs, in some embodiments, toward the PA side of the original interface suggesting that the megadalton macromolecules diffuse into the small molecule solution. The switch in fiber orientation by nearly 90° is, in some embodiments, initiated by reptation of the HA molecules through the mesh of amorphous and parallel fiber regions which then end up nucleating hybrid fibers aligned perpendicular to the interface (FIGS. 4B and 4D). Diffusion of the large macromolecules is driven, in some embodiments, by the osmotic pressure imbalance between the PA and HA solutions. This imbalance is due, for example, to the preservation of macroscopic electroneutrality; since there is a greater charge density in a high molecular weight polyelectrolyte, there is a greater number of ions required to neutralize the total charge in the HA solution compared to the PA solution. This difference in ion concentration results, for example, in an excess osmotic pressure of ions in the HA compartment.

Using Poisson-Boltzman theories applied to the cell model of polyelectrolytes (see, e.g., M. Deserno, H. H. von Grunberg, Phys Rev E Stat Nonlin Soft Matter Phys 66, 011401 (July, 2002); C. Holm, P. Kâekicheff, R. Podgornik, North Atlantic Treaty Organization. Scientific Affairs Division., Electrostatic effects in soft matter and biophysics, NATO science series. Series II, Mathematics, physics, and chemistry; v. 46 (Kluwer Academic Publishers, Dordrecht, [Netherlands]; Boston, 2001), pp. xvi, 509), the difference in osmotic pressure between the two solutions is described by the following expression, $$\Delta\Pi \equiv \Pi_{HA} - \Pi_{PA} = k_B T \sum_i n_i \left( e^{-\frac{ev_i\psi(R)}{k_B T}} - 1 \right)$$

where $n_i$ and $v_i$ are concentration and valence of mobile ions, $\psi(r)$ is a local electrostatic potential and R is the Wigner cell radius. The electrostatic potential is proportional to the measured zeta potential, $\zeta$, and has a direct effect on the osmotic pressure difference as follows, $$\Delta\Pi \zeta^2 \sum_i \frac{n_i(ev_i)^2}{2k_B T} \geq 0.$$

A difference in zeta potential between the two components results, in some embodiments, in a large difference in osmotic pressure. Under excess osmotic pressure in the HA compartment, macromolecules rather than the small PA molecules diffuse through the initially formed contact layer. The required elongated conformation of the HA molecule for diffusion through the pores of the contact layer also creates, in some embodiments, an entropic barrier that can be overcome only when the excess osmotic pressure dominates. The diffusion driven by the excess osmotic pressure, $\Delta\Pi$, is described by the Smoluchowski equation, $$\frac{\partial}{\partial t} w(s,t) = D_o \frac{\partial}{\partial s} \left[ \frac{\partial}{\partial s} + \frac{\Delta\Pi\lambda b^2 - F}{k_B T} \right] w(s,t)$$

where $D_o$ is the bare diffusion coefficient, $\lambda$ is the thickness of the diffusive barrier, b is the HA monomer size, $F \propto_B T \ln(N-s)$ is the entropic free energy of a polymer chain of N repeats with s monomer units that have passed through the membrane, and w(s,t) determines the probability of having a segment of s monomers at time t through the membrane. The released free ends of HA molecules, after complete reptation through the contact layer, produce, in some embodiments, polymer "stubs" at the surface of the contact layer (FIG. 4D) that attract the oppositely charged PA molecules (FIG. 4B) and nucleate the self-assembly of perpendicularly oriented nanofibers (FIG. 4C). Growth of the nanofibers occurs by attraction of PA aggregates at the base of the polymer stubs as "new" HA segments continue to penetrate through the parallel fiber mesh (FIGS. 4C and E). Extensive self-assembly and elongation of these fibers, in some embodiments, eventually lead to a crowding effect that further increases the orientational order or alignment in this region over time (FIG. 4F) as demonstrated earlier by microscopy (FIG. 2C).

In some embodiments, self-assembly of the hierarchically ordered system involves a cascading set of events with elements of both static and dynamic self-assembly. Once the contact layer is formed by static self-assembly, the electrostatic potential difference, in some embodiments, is large enough to cause an osmotic pressure imbalance to drive polymer diffusion through the contact layer. Self-assembly of the hybrid nanofibers nucleated by polymer chain segments penetrating into the PA solution releases condensed counterions that subsequently, in some embodiments, migrate to the polymer side, given the high affinity of polyelectrolytes for small ions. The excess osmotic pressure difference is sustained, in some embodiments, in dynamic fashion to continuously pump additional polymer chains through the barrier.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A composition comprising a self-assembling membrane, said self-assembling membrane comprising:
    a first component comprising a charged high molecular weight macromolecule;
    a second component comprising a self-assembling molecule of opposite charge;
    wherein said first and second components have opposite zeta potential values;
    wherein said first and second components interact to form said self-assembling membrane;
    wherein said self-assembling membrane comprises regions of nanofiber bundles;
    wherein said self-assembling membrane encapsulates living cells.

2. The composition of claim 1, wherein said charged macromolecule comprises a positively or negatively charged high molecular weight polysaccharide.

3. The composition of claim 2, wherein said charged polysaccharide is hyaluronic acid.

4. The composition of claim 1, wherein said self-assembling molecules are peptide-based molecules.

5. The composition of claim 4, wherein said self-assembling peptide molecules are amphiphilic.

6. The composition of claim 5, wherein said self-assembling peptide molecules comprise one or more alkyl tails attached to a charged peptide sequence.

7. The composition of claim 1, wherein said self-assembling membrane is a self-sealing sac.

8. The composition of claim 1, wherein said self-assembling membrane is a self-sealing film.

9. The composition of claim 1, wherein said self-assembling membrane is a continuous string.

10. The composition of claim 1, wherein said self-assembling membrane encapsulates one or more bioactive agents.

11. The composition of claim 10, wherein said one or more bioactive agents are selected from the group consisting of a dye, a probe, a nucleic acid, an enzyme, an oligonucleotide, a label, a protein, a polypeptide, a lipid, a glycoprotein, a glycolipid, pilocarpine, hydrocortisone, prednisolone, cortisone, diclofenac sodium, indomethacin, 6∞-methyl-prednisolone, corticosterone, dexamethasone, prednisone, penicillin, cephalosporins, bacitracin, tetracycline, doxycycline, gentamycin, chloroquine, vidarabine, salicylic acid, acetaminophen, ibuprofen, naproxen, piroxicam, flurbiprofen, morphine, cocaine, lidocaine, benzocaine, leuprolide acetate, nafarelin, a ganglioside, a nerve growth factor, fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-alpha), transforming growth factor-beta (TGF-beta), epidermal growth factor (EGF), fibroblast growth factor (FGF), interleukin-1 (IL-1), vascular endothelial growth factor (VEGF) and keratinocyte growth factor (KGF), dried bone material, methotrexate, 5-fluorouracil, adriamycin, vinblastine, cisplatin, tumor-specific antibodies conjugated to toxins, tumor necrosis factor, progesterone, testosterone, follicle stimulating hormone (FSH) (birth control, fertility-enhancement), insulin, diphenhydramine, papaverine, streptokinase, isopropamide iodide, metaproternal sulfate, aminophylline, theophylline, niacin, minoxidil, B-adrenergic blocking agent, dopamine, risperidone, naltrexone, naloxone, buprenorphine, cross-linked alginates, gelatin, collagen, cross-linked collagen, collagen derivatives, succinylated collagen or methylated collagen, cross-linked hyaluronan, chitosan, chitosan derivatives, methylpyrrolidone-chitosan, cellulose, cellulose derivatives such as cellulose acetate or carboxymethyl cellulose, dextran derivatives such carboxymethyl dextran, starch and derivatives of starch such as hydroxyethyl starch, other glycosaminoglycans and their derivatives, other polyanionic polysaccharides or their derivatives, polylactic acid (PLA), polyglycolic acid (PGA), a copolymer of a polylactic acid and a polyglycolic acid (PLGA), lactides, glycolides, and other polyesters, polyoxanones and polyoxalates, copolymer of poly(bis(p-carboxyphenoxy)propane)anhydride (PCPP) and sebacic acid, poly(L-glutamic acid), poly(D-glutamic acid), polyacrylic acid, poly(DL-glutamic acid), poly(L-aspartic acid), poly(D-aspartic acid), poly(DL-aspartic acid), polyethylene glycol, copolymers of the polyamino acids with polyethylene glycol, polypeptides, such as, collagen-like, silk-like, and silk-elastin-like proteins, polycaprolactone, poly (alkylene succinates), poly(hydroxy butyrate) (PHB), poly (butylene diglycolate), nylon-2/nylon-6-copolyamides, polydihydropyrans, polyphosphazenes, poly(ortho ester), poly(cyano acrylates), polyvinylpyrrolidone, polyvinylalcohol, poly casein, keratin, myosin, and fibrin.

12. The composition of claim 1, wherein said living cells are selected from the group consisting of fibroblasts, hepatocytes, chondrocytes, stem cells, bone marrow, muscle cells, cardiac myocytes, neuronal cells, pancreatic islet cells, tumor cells, chondrocytes, stem cells, epithelial cells, cells from neural lineages, cells derived from the liver, endothelial cells, cardiac cells, muscle cells, and osteoblasts.

13. The composition of claim 1, wherein said regions of nanofiber bundles are alternating regions of nanofiber bundles.

14. The composition of claim 13, wherein said alternating regions of nanofiber bundles are perpendicularly opposed.

15. The composition of claim 1, wherein the second component has a pH value less than or equal to about 11.

16. The composition of claim 1, wherein the first component has a pH value greater than or equal to about 3.

17. The composition of claim 1, wherein the pH of the first component and the second component are selected from the group consisting of (1) the pH of the first component is greater than or equal to about 1 and the pH of the second component is less than or equal to about 11; (2) the pH of the first component is greater than or equal to about 3 and the pH of the second component is between about 1 and 11; and (3) the pH of the first component is greater than or equal to about 10 and the second component is less than or equal to about 2.

* * * * *